US006821927B1

(12) United States Patent
Krüger et al.

(10) Patent No.: US 6,821,927 B1
(45) Date of Patent: Nov. 23, 2004

(54) HYDROXAMIC ACID DERIVATIVES

(75) Inventors: Bernd-Wieland Krüger, Bergisch Gladbach (DE); Herbert Gayer, Monheim (DE); Peter Gerdes, Aachen (DE); Fritz Maurer, Monheim (DE); Ulrich Heinemann, Leichlingen (DE); Martin Vaupel, Leichlingen (DE); Astrid Mauler-Machnik, Leichlingen (DE); Ulrike Wachendorff-Neumann, Neuwied (DE); Gerd Hänssler, Leverkusen (DE); Karl-Heinz Kuck, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 115 days.

(21) Appl. No.: 10/130,388

(22) PCT Filed: Nov. 6, 2000

(86) PCT No.: PCT/EP00/10918

§ 371 (c)(1),
(2), (4) Date: May 14, 2002

(87) PCT Pub. No.: WO01/36393

PCT Pub. Date: May 25, 2001

(30) Foreign Application Priority Data

Nov. 17, 1999 (DE) .......................... 199 55 130

(51) Int. Cl.$^7$ .................... A01N 43/54; C07D 239/02
(52) U.S. Cl. .................... 504/243; 544/319
(58) Field of Search .................. 544/319; 514/269; 504/243

(56) References Cited

U.S. PATENT DOCUMENTS 6,235,743 B1 * 5/2001 Gayer et al. .............. 514/269

6,251,899 B1   6/2001 Gerdes et al. ............ 514/229.2

FOREIGN PATENT DOCUMENTS

| GB | 2249092 | 4/1992 |
|----|---------|--------|
| WO | 94/05626 | 3/1994 |
| WO | 95/20570 | 8/1995 |
| WO | 98/21189 | 5/1998 |
| WO | 00/10970 | 3/2000 |
| WO | 00/71504 | 11/2000 |
| WO | 00/78732 | 12/2000 |
| WO | 00/78733 | 12/2000 |

OTHER PUBLICATIONS

Chem. Ber. 90, (month unavailable) 1957, pp. 942–951, Hellmut Bredereck, Rudolf Gompper Und Gerhard Morlack, Formamid–Reaktionen. VIII[1]), Eine Neue Pyridmid-in–Synthese[2]).

Hawley's Condensed Chemical Dictionary, 12$^{th}$ ed., Richard J. Lewis, Sr., © 1993 by Van Nostrand Reinhold. p. 594.*

Concise Chemical Dictionary, edited by Drs. Hans–Dieter Jakubke and Hans Jeschkeit, © 1993 by Walter de Gruyter & Co., p. 490.*

McGraw–Hill Dictionary of Chemical Terms, 3$^{rd}$ ed. edited by Sybil P. Parker, © 1984 McGraw–Hill, Inc., p. 200.*

* cited by examiner

*Primary Examiner*—Richard L. Raymond
*Assistant Examiner*—Zachary C. Tucker
(74) *Attorney, Agent, or Firm*—Richard E. L. Henderson; Raymond J. Harmuth

(57) ABSTRACT

The invention relates to novel hydroxamic acid derivatives, to a plurality of processes for their preparation and to their use as pesticides.

11 Claims, No Drawings

HYDROXAMIC ACID DERIVATIVES

This application was filed under 35 U.S.C. 371, and is the U.S. National Stage of PCT/EP00/10918, filed 6, Nov. 2000.

The invention relates to novel hydroxamic acid derivatives to a plurality of processes for their preparation and to their use as pesticides.

Certain hydroxamic acid derivatives having a similar substitution pattern, and their fungicidal action, are already known (compare, for example, WO 95-20570)). However, in particular at low application rates and concentrations, the activity of these prior-art compounds is not entirely satisfactory in all areas of use.

This invention, accordingly, provides the novel hydroxamic acid derivatives of the general formula (I)

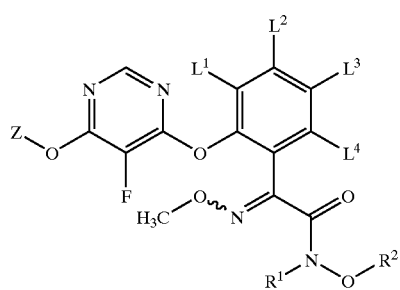

(I)

in which
Z represents in each case substituted or unsubstituted cycloalkyl, aryl or heterocyclyl,
$L^1$, $L^2$, $L^3$ and $L^4$ are identical or different and independently of one another each represent hydrogen, halogen, cyano, nitro, in each case optionally halogen-substituted alkyl, alkoxy, alkylthio, alkylsulfinyl or alkylsulfonyl,
$R^1$ represents hydrogen or alkyl and
$R^2$ represents hydrogen, alkyl, alkylcarbonyl, alkoxycarbonyl or arylcarbonyl.

In the definitions, the saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino. Unless stated otherwise, preference is given to hydrocarbon chains having 1 to 6 carbon atoms.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl, which may optionally also be fuzed to further aliphatic or heterocyclic rings. Thus, aryl also represents tetralinyl, indolyl or benzofuranyl, for example; however, the point of attachment is at the phenyl moiety.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen or sulfur. If the ring contains a plurality of oxygen atoms, these are not adjacent. The cyclic compounds may optionally form a polycyclic ring system with other carbocyclic or heterocyclic fuzed-on or bridged rings. Preference is given to mono- or bicyclic ring systems, in particular to mono- or bicyclic aromatic ring systems.

Cycloalkyl represents saturated carbocyclic cyclic compounds which may optionally form a polycyclic ring system with other carbocyclic fuzed-on or bridged rings.

A polycyclic ring system may be attached to a heterocyclic ring or a fuzed-on carbocyclic ring. The heterocyclyl radical described in this manner may also be mono- or polysubstituted, preferably by methyl, ethyl, halogen or chlorine. Preference is given to mono- or bicyclic ring systems, in particular to mono- or bicyclic ring systems.

Halogenoalkoxy represents partially or fully halogenated alkoxy. In the case of polyhalogenated halogenoalkoxy, the halogen atoms can be identical or different. Preferred halogen atoms are fluorine and, in particular, chlorine. If the halogenoalkoxy carries other substituents, the maximum possible number of halogen atoms is reduced to the different free valencies.

Halogenoalkyl represents partially or fully halogenated alkyl. In the case of polyhalogenated halogenoalkyl, the halogen atoms can be identical or different.

Preferred halogen atoms are fluorine and chlorine, in particular fluorine. If the halogenoalkyl carries other substituents, the maximum possible number of halogen atoms is reduced to the remaining free valencies.

Furthermore, it has been found that the novel hydroxamic acid derivatives of the general formula (I) are obtained when
a) carboxylic acid derivatives of the formula (II)

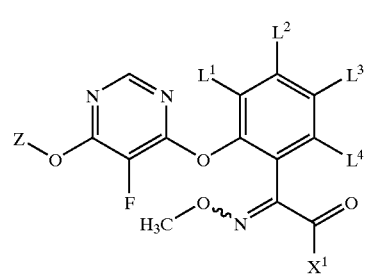

(II)

in which
$L^1$, $L^2$, $L^3$, $L^4$ and Z are as defined above and
$X^1$ represents halogen, are reacted with a substituted or unsubstituted hydroxylamine derivative of the general formula (III)

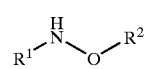

(III)

in which
$R^1$ and $R^2$ are as defined above,
if appropriate in the presence of a diluent and if appropriate in the presence of an acid acceptor, or when
b) compounds of the general formula (I) where $R^2$ is hydrogen are reacted with a halogen compound of the general formula (IV)

(IV)

in which
$R^{2'}$ represents alkyl, alkylcarbonyl, alkoxycarbonyl or arylcarbonyl and
$X^2$ represents halogen, if appropriate in the presence of a diluent, if appropriate in the presence of an acid acceptor.

Finally, it has been found that the novel hydroxamic acid derivatives of the general formula (I) have very strong very strong activity against pests of plants.

If appropriate, the compounds according to the invention can be present as mixtures of different possible isomeric forms, in particular of stereoisomers, such as, for example, E and Z. What is claimed are both the E and the Z isomers, and also any mixtures of these isomers.

The invention preferably provides compounds of the formula (I) in which

Z represents cycloalkyl having 3 to 7 carbon atoms which is optionally mono- to disubstituted by halogen, alkyl or hydroxyl;

represents heterocyclyl having 3 to 7 ring members which is optionally substituted by alkyl having 1 to 4 carbon atoms;

or represents phenyl or naphthyl, each of which is optionally mono- to tetrasubstituted by identical or different substituents, where the possible substituents are preferably selected from the list below:

halogen, cyano, nitro, amino, hydroxyl, formyl, carboxyl, carbamoyl, thiocarbamoyl;

in each case straight-chain or branched alkyl, hydroxyalkyl, oxoalkyl, alkoxy, alkoxyalkyl, alkylthioalkyl, dialkoxyalkyl, alkylthio, alkylsulfinyl or alkylsulfonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the hydrocarbon chains in question;

cycloalkyl or cycloalkyloxy having in each case 3 to 6 carbon atoms;

in each case doubly attached alkylene having 3 to 4 carbon atoms, oxyalkylene having 2 or 3 carbon atoms or dioxyalkylene having 1 or 2 carbon atoms, each of which radicals is optionally mono- to tetrasubstituted by identical or different radicals from the group consisting of fluorine, chlorine, oxo, methyl, trifluoromethyl and ethyl;

or a grouping

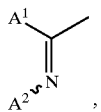

in which $A^1$ represents hydrogen, hydroxyl or alkyl having 1 to 4 carbon atoms or cycloalkyl having 1 to 6 carbon atoms and $A^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms, and also phenyl, phenoxy, phenylthio, benzoyl, benzoylethenyl, cinnamoyl, heterocyclyl or phenylalkyl, phenylalkyloxy, phenylalkylthio, or heterocyclylalkyl, having in each case 1 to 3 carbon atoms in the alkyl moieties in question, each of which radicals is optionally mono- to trisubstituted in the cyclic moiety by halogen and/or straight-chain or branched alkyl or alkoxy having 1 to 4 carbon atoms, $L^1, L^2, L^3$ and $L^4$ are identical or different and independently of one another each represents hydrogen, halogen, cyano, nitro, or alkyl, alkoxy, alkylthio, alkylsulfinyl or alkylsulfonyl having in each case 1 to 6 carbon atoms, each of which radicals is optionally substituted by 1 to 5 halogen atoms, $R^1$ represents hydrogen or alkyl and $R^2$ represents hydrogen, alkyl, alkylcarbonyl, alkoxycarbonyl or arylcarbonyl.

The invention relates in particular to compounds of the formula (I) in which

Z represents cyclopentyl or cyclohexyl, each of which is optionally mono- to disubstituted by fluorine, chlorine, methyl, ethyl or hydroxyl;

represents furyl, pyridyl or thienyl which is optionally substituted by methyl or ethyl;

or represents phenyl or naphthyl, each of which is optionally mono- to tetrasubstituted by identical or different substituents, where the possible substituents are preferably selected from the list below:

fluorine, chlorine, bromine, iodine, cyano, nitro, amino, hydroxyl, formyl, carboxyl, carbamoyl, thiocarbamoyl, methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimetylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methoxymethyl, ethoxymethyl, methylthio, ethylthio, n- or i-propylthio, methylsulfinyl, ethylsulfinyl, methyl-sulfonyl or ethylsulfonyl, methylthiomethyl, ethylthiomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulfinyl or trifluoromethylsulfonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl or a grouping

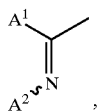

where
A¹ represents hydrogen, methyl or hydroxyl and
A² represents hydroxyl, methoxy, ethoxy, amino, methylamino, phenyl, benzyl or hydroxyethyl, and also phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the cyclic moiety by halogen and/or straight-chain or branched alkyl or alkoxy having 1 to 4 carbon atoms,
$L^1, L^2, L^3$ and $L^4$ are identical or different and independently of one another each represent hydrogen, methyl, ethyl, n- or i-propyl, n-, i-, s- or t-butyl,
$R^1$ represents hydrogen or alkyl,
$R^2$ represents hydrogen, alkyl, alkylcarbonyl, alkoxycarbonyl or arylcarbonyl.

In a very particularly preferred group of compounds, Z represents optionally substituted phenyl.

Particular preference is given to compounds of the formula (I) in which $R^1$ represents hydrogen and, in particular, methyl.

Particular preference is given to compounds of the formula (I) in which Z represents optionally substituted phenyl, where the substituents are preferably selected from the list below: halogen, cyano, in each case straight-chain or branched alkyl, alkylthio, alkylthioalkyl, halogenoalkyl, halogenothioalkyl.

In a further very particularly preferred group of compounds
$L^1$, $L^2$ and $L^3$ represent hydrogen and
$L^4$ represents hydrogen or represents methyl.

The invention relates particularly preferably to compounds of the formula (I) in which
Z represents phenyl which is in each case optionally mono- to trisubstituted by identical or different substituents, where the substituents are selected from the list below: fluorine, chlorine, $C_1$–$C_4$-alkyl or cyano,
$L^1$, $L^2$, $L^3$ and $L^4$ represent hydrogen,
$R^1$ represents $C_1$–$C_4$-alkyl, and
$R^2$ represents hydrogen or methyl.

The general or preferred radical definitions given above apply both to the end products of the formula (I) and, correspondingly, to the starting materials or intermediates required in each case for the preparation.

The specific radical definitions given in the combinations or preferred combinations of radicals in question for these radicals are, independently of the combination of radicals given in each case, also replaced by any radical definitions of other preferred ranges.

The formula (II) provides a general definition of the carboxylic acid derivatives required as starting materials for carrying out the process a) according to the invention. In this formula (II), $L^1, L^2, L^3, L^4$ and Z preferably or in particular have those meanings which have already been mentioned in connection with the description of the compounds of the formula (I) according to the invention as being preferred or as being particularly preferred for $L^1, L^2, L^3, L^4$ and Z. $X^1$ represents halogen, preferably chlorine.

The starting materials of the formula (II) have hitherto not been disclosed and, as novel substances, also form part of the subject-matter of the present application.

They are obtained (process c) when carboxylic acids of the general formula (V)

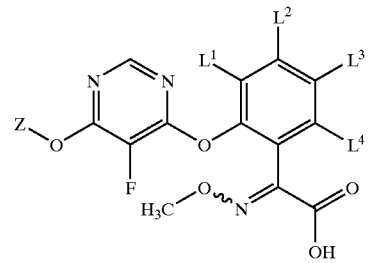

in which
$L^1, L^2, L^3, L^4$ and Z are as defined above
are reacted with a halogenating agent, if appropriate in the presence of a diluent and if appropriate in the presence of a catalyst.

The formula (V) provides a general definition of the carboxylic acids required as starting materials for carrying out the process c) according to the invention. In this formula (V), $L^1, L^2, L^3, L^4$ and Z preferably or in particular have those meanings which have already been mentioned in connection with the description of the compounds of the formula (I) according to the invention as being preferred or as being particularly preferred for $L^1, L^2, L^3, L^4$ and Z.

The starting materials of the formula (V) have hitherto not been disclosed and, as novel substances, also from part of the subject-matter of the present application.

They are obtained (process d) when carboxylic acid esters of the general formula (VI)

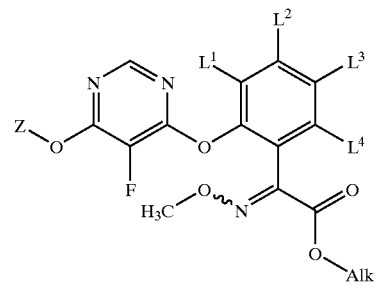

in which
$L^1, L^2, L^3, L^4$ and Z have the meanings given above and
Alk represents alkyl
are reacted with an acid, if appropriate in the presence of a diluent and if appropriate in the presence of a catalyst.

The formula (VI) provides a general definition of the carboxylic acid esters required as starting materials for carrying out the process d) according to the invention. In this formula (VI), $L^1, L^2, L^3, L^4$ and Z preferably or in particular have those meanings which have already been mentioned in connection with the description of the compounds of the formula (I) according to the invention as being preferred or as being particularly preferred for $L^1, L^2, L^3, L^4$ and Z. Alk represents alkyl, preferably methyl or ethyl.

The starting materials of the formula (VI) have hitherto not been disclosed and, as novel substances, also form part of the subject-matter of the present application.

The starting materials of formula (VI) can be obtained (process e) by reacting 2-(2-hydroxy-phenyl)-2-alkoxyiminoacetic esters of the general formula (VII)

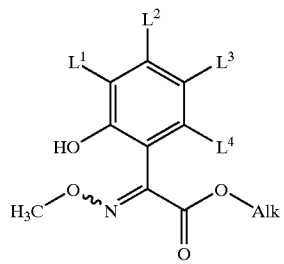
(VII)

in which

Alk, $L^1$, $L^2$, $L^3$ and $L^4$ are as defined above with a fluoropyrimidine of the general formula (VIII)

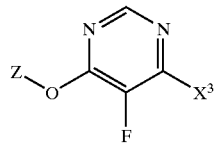
(VIII)

in which

Z is as defined above and $X^3$ represents halogen, if appropriate in the presence of a diluent, such as, for example, acetonitrile, if appropriate in the presence of an acid acceptor, such as, for example, calcium carbonate.

The formula (VII) provides a general definition of the 2-(2-alkoxy-phenyl)-2-methoxyiminoacetic esters required as starting materials for carrying out the process e). In this formula (VII), Alk, $L^1$, $L^2$, $L^3$ and $L^4$ preferably or in particular have those meanings which have already been mentioned in connection with the description of the compounds of the formula (VI) according to the invention as being preferred or as being particularly preferred for Alk, $L^1$, $L^2$, $L^3$ and $L^4$.

The starting materials of formula (VII) are known and can be prepared by known processes (compare, for example, WO-A 94-05626, GB-A 2249092)

The formula (VIII) provides a general definition of the fluoropyrimidines further required as starting materials for carrying out the process e). In this formula (VEII) Z preferably or in particular has that meaning which has already been mentioned in connection with the description of the compounds of the formula (I) according to the invention as being preferred or as being particularly preferred for Z. $X^3$ represents halogen, preferably fluorine or chlorine.

The starting materials of the formula (Vffl) are known and/or can be prepared by known methods (compare, for example, DE 19737723; Chem. Ber., 90<1957>942, 951).

Suitable halogenating agents for carrying out the process c) according to the invention are all reagents capable of exchanging hydroxyl groups attached on carbon for halogens. Examples which may be mentioned are: phosgene, oxalyl chloride, phosphorus trichloride, phosphorus tribromide, phosphorus pentachloride, phosphorus oxychloride, thionyl chloride or thionyl bromide. The halogenating agents are known chemicals for synthesis.

The formula (III) provides a general definition of the hydroxylamine derivatives furthermore required as starting materials for carrying out the process a) according to the invention. In this formula (III), $R^1$ and $R^2$ preferably or in particular have those meanings which have already been mentioned in connection with the description of the compounds of the formula (I) according to the invention as being preferred or as being particularly preferred for $R^1$ and $R^2$.

The starting materials of the formula (HI) are generally customary chemicals for synthesis.

The hydroxamic acid derivatives of the general formula (I) where $R^2$ is hydrogen, which hydroxamic acid derivatives are required as starting materials for carrying out the process b) according to the invention, are compounds according to the invention and can be prepared by process a).

The formula (IV) provides a general definition of the halogen compounds furthermore required as starting materials for carrying out process a) according to the invention. In this formula (IV) $R^2$ preferably or in particular has those meanings which have already been mentioned in connection with the description of the compounds of the formula (I) according to the invention as being preferred or as being particularly preferred for $R^2$. $X^2$ represents halogen, preferably chlorine.

The starting materials of the formula (IV) are generally customary chemicals for synthesis.

Suitable diluents for carrying out the processes a) and b) according to the invention are all inert organic solvents. These include, by way of example and by way of preference, ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulfoxides, such as dimethyl sulfoxide; or sulfones, such as sulfolane.

The processes a) and b) according to the invention are, if appropriate, carried out in the presence of a suitable acid acceptor. Suitable acid acceptors are all customary inorganic or organic bases. These include, by way of example and by way of preference, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a) and b) according to the invention the reaction temperatures can be varied within a relatively wide range. In general, the processes are carried out at temperatures from −20° C. to 100° C., preferably temperatures from −10° C. to 80° C.

For carrying out the process a) according to the invention for preparing the compounds of the formula (I), in general from 0.5 to 15 mol, preferably from 0.8 to 8 mol, of substituted hydroxylamine derivative of the formula (III) are employed per mole of the carboxylic acid derivative of the formula (II).

For carrying out the process b) according to the invention for preparing the compounds of the formula (I), in general from 0.5 to 15 mol, preferably from 0.8 to 8 mol, of a halogen compound of the general formula (IV) are employed per mole of the hydroxamic acid derivative of the formula (I) where $R^2$ is hydrogen.

Suitable diluents for carrying out the process c) according to the invention are all inert organic solvents. These include, by way of example and by way of preference, aliphatic, alicyclic or aromatic hydrocarbons, such as, for example, petroleum ether, hexane, heptane, cyclohexane, methylcyclohexane, benzene, toluene, xylene or decaline, or halogenated hydrocarbons, such as, for example, chlorobenzene, dichlorobenzene, dichloromethane, chloroform, carbon tetrachloride, dichloroethane or trichloroethane.

Suitable catalysts for carrying out the process c) according to the invention are, for example, pyridine or dimethylformamide.

When carrying out the process c) according to the invention, the reaction temperatures can be varied within a relatively wide range. In general, the process is carried out at temperatures from −10° C. to 100° C., preferably at temperatures from 0° C. to 80° C.

For carrying out the process c) according to the invention for preparing the compounds of the formula (II), in general from 1 to 15 mol, preferably from 2 to 8 mol, of halogenating agent are employed per mole of the carboxylic acid of the formula (V).

Suitable diluents for carrying out the process d) according to the invention are all inert organic solvents. These include, by way of example and by way of preference, aliphatic, alicyclic or aromatic hydrocarbons, such as, for example, petroleum ether, hexane, heptane, cyclohexane, methylcyclohexane, benzene, toluene, xylene or decaline, or halogenated hydrocarbons, such as, for example, chlorobenzene, dichlorobenzene, dichloromethane, chloroform, carbon tetrachloride, dichloroethane or trichloroethane.

The process d) according to the invention is, if appropriate, carried out in the presence of an acid. Suitable acids are all inorganic and organic protonic acids including, by way of example and by way of preference, Lewis acids, and also all polymeric acids. These include, for example, hydrogen chloride, sulfuric acid, phosphoric acid, formic acid, acetic acid, trifluoroacetic acid, methanesulfonic acid, trifluoromethanesulfonic acid, toluenesulfonic acid, boron trifluoride (also as etherate), boron tribromide, aluminum trichloride, titanium tetrachloride, tetrabutylorthotitanate, zinc chloride, iron (III) chloride, antimony pentachloride, acidic ion exchangers, acidic alumina and acidic silica gel.

When carrying out the process according to the invention, the reaction temperatures can be varied within a relatively wide range. In general, the process is carried out at temperatures from −50° C. to 80° C., preferably at temperatures from −20° C. to 50° C.

For carrying out the process d) according to the invention for preparing the compounds of the formula (V), in general from 1 to 15 mol, preferably from 2 to 8 mol, of acid are employed per mole of the carboxylic acid ester of the formula (VI).

All processes according to the invention are generally carried out under atmospheric pressure. However, it is also possible to operate under elevated or reduced pressure in general between 0.1 bar and 10 bar.

The practice of the reaction and work-up and isolation of the reaction products are carried out by generally customary processes (compare also the Preparation Examples).

The substances according to the invention have potent microbiocidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*;

*Pythium* species, such as, for example, *Pythium ultimum*;

*Phytophthora* species, such as, for example, *Phytophthora infestans*;

*Pseudoperonospora* species, such as, for example, *Pseudoperonospora humuli* or

*Pseudoperonospora cubensis*;

*Plasmopara* species, such as, for example, *Plasmopara viticola*;

*Bremia* species, such as, for example, *Bremia lactucae*;

*Peronospora* species, such as, for example, *Peronospora pisi* or *P. brassicae*;

*Erysiphe* species, such as, for example, *Erysiphe graminis*;

*Sphaerotheca* species, such as, for example, *Sphaerotheca fuliginea*;

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea* (conidial form: *Drechslera*, syn: *Helminthosporium*);

*Cochliobolus* species, such as, for example, *Cochliobolus sativus* (conidial form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*; *Pellicularia* species, such as, for example, *Pellicularia sasakii*; *Pyricularia* species, such as, for example, *Pyricularia oryzae*; *Fusarium* species, such as, for example, *Fusarium culmorum*; *Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The fact that the active compounds are well tolerated by plants at the concentrations required for controlling plant diseases permits the treatment of above-ground parts of plants, of propagation stock and seeds, and of the soil.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned by way of example being leaves, needles, stems, trunks, flowers, fruit bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds according to the invention can be employed particularly successfully for controlling cereal diseases, such as, for example, against Erisiphe or *Puccinia* species, diseases in viticulture and fruit and vegetable growing such as, for example, against *Venturia, Sphaerotheca*, phytophtora and *Plasmopara* species, or rice diseases, such as, for example, against *Pyricularia* species.

The active compounds according to the invention are also suitable for increasing the yield of crops. In addition, they show reduced toxicity and are well tolerated by plants.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents.

Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing partners are the following:
Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminum, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole, imazalil, imibenconazole, iminoctadine, iminoctadine albesilate, ininoctadine triacetate, iodocarb, ipconazole, iprobenfos (DBP), iprodione, irumamycin, isoprothiolane, isovaledione, kasugamycin, kresoxim-methyl, copper preparations, such as: copper hydroxide, copper naphthenate, copper oxychloride, copper sulfate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulfur and sulfur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-C-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

β-(5-methyl-1,3-dioxan-5-yl)-β-[[4-(trifluoromethyl)-phenyl]-methylene]1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulfonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulfonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo 1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulfate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide.

N-(2,6-dimethylphenyl)-2-methoxy-N-(tetrahydro-2-oxo-3-furanyl)-acetamide,

N-(2,6-dimethylphenyl)-2-methoxy-N-(tetrahydro-2-oxo-3-thienyl)-acetamide,

N-(2-chloro-4-nitrophenyl)-4-methyl-3-nitro-benzenesulfonamide,

N-(4-cyclohexylphenyl)-1,4,5,6-tetrahydro-2-pyrimidineamine,

N-(4-hexylphenyl)-1,4,5,6-tetrahydro-2-pyrimidineamine,

N-(5-chloro-2-methylphenyl)-2-methoxy-N-(2-oxo-3-oxazolidinyl)-acetamide,

N-(6-methoxy-3-pyridinyl)-cyclopropanecarboxamide,

N-[2,2,2-trichloro-1-[(chloroacetyl)-amino]-ethyl]-benzamide,

N-[3-chloro-4,5-bis-(2-propinyloxy)-phenyl]-N'-methoxy-methanimidamide,

N-formyl-N-hydroxy-DL-alanine sodium salt,

O,O-diethyl [2-(dipropylamino)-2-oxoethyl]-ethylphosphoramidothioate,

O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoat, oxamyl, oxydemethon M,
*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI5302
zeta-cypermethrin, zolaprofos
(1R-cis)-[5-(phenylmethyl)-3-furanyl]-methyl-3-[(dihydro-2-oxo-3(2H)-furanylidene)-methyl]
-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-diemthylethyl) phenyl]4,5-dihydro-oxazole,
2-(acetlyoxy)-3-docecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoranridothioate.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, for example against *Candida* species, such as *Candida albicans, Candida glabrata* such as Epidermophyton floccosum, *Aspergillus* species, such as *Aspergillus niger* and *Aspergillus* fumigatus, *Trichophyton* species, such as *Trichophyton mentagrophytes*, Microsporon species such as Microsporon canis and audouinii. The list of these fungi in no way limits the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The examples below serve to illustrate the invention. However, the invention is not limited to the examples.

PREPARATION EXAMPLES

Example 1

2-(2-{[6-(2-Chlorophenoxy)-5-fluoro-4-pyrimidinyl]oxy} phenyl)-N-hydroxy-2-methoxyimino)-N-methylacetamide 47.2 g (0.47 mol) of triethylamine are initially added to a mixture of 32.45 g (0.39 mol) of N-methylhydroxylamine hydrochloride in 400 ml of tetrahydrofuran, the mixture is cooled to 0° C., and at this temperature, a solution of 33.6 g (0.078 mol) of 2-{2-[6-(2-chlorophenoxy)-5-fluoro-pyrimidin-4-yloxy]-phenyl}-2-methoxyiminoacetyl chloride in 50 ml of tetrahydrofuran is then added dropwise over a period of 1 hour. Without further cooling, stirring is continued for 18 hours. The reaction mixture is poured into 2 l of water and extracted 3 times with in each case 400 ml of ethyl acetate. The combined organic phases are dried over sodium sulfate and concentrated under reduced pressure. The residue is stirred with diisopropyl ether, filtered off with suction and dried. This gives 13.2 g (38% of theory) of 2-(2-{[6-(2-chlorophenoxy)-5-fluoro-4-pyrimidinyl]oxy} phenyl)-N-hydroxy-2-(methoxyimino)-N-methylacetamide.
HPLC: logP=2.82

Example 2

2-(2-{[6-(2-Chlorophenoxy)-5-fluoro-4-pyrimidinyl]oxy} phenyl)-N-hydroxy-2-(methoxyimino)-acetamide 1.4 g (0.014 mol) of triethylamine are initially added to a mixture of 0.8 g (0.012 mol) of hydroxylamine hydrochloride in 20 ml of tetrahydrofuran, the mixture is cooled to 0° C., and at this temperature, a solution of 1 g (0.0023 mol) of 2-{2-[6-(2-chlorophenoxy)-5-fluoro-pyrimidin-4-yloxy]-phenyl}-2-methoxyiminoacetyl chloride in 10 ml of tetrahydrofuran is then added dropwise. Without further cooling, stirring is continued for 18 hours. The reaction mixture is poured into 100 ml of 1 N hydrochloric acid and extracted 3 times with in each case 100 ml of ethyl acetate. The combined organic phases are dried over sodium sulfate and concentrated under reduced pressure. The residue is chromatographed on silica gel using cyclohexane/ethyl acetate (4:1). This gives 0.3 g (30% of theory) of 2-(2-{[6-(2-chlorophenoxy)-5-fluoro-4-pyrimidinyl]oxy} phenyl)-N-hydroxy-2-(methoxyimino)-acetamide.
HPLC: logP=2.56

Example 3

N-(Acetyloxy)-2-(2-{[6-(2-chlorophenoxy)-5-fluoro-4-pyrimidinyl]oxy}phenyl)-2-(methoxyimino)-N-methylacetamide 0.12 g (0.0012 mol) of triethylamine is initially added to a mixture of 0.4 g (0.0009 mol) of 2-(2-{[6-(2-chlorophenoxy)-5-fluoro-4-pyrimidinyl]oxy}phenyl)-N-hydroxy-2-(methoxyimino)-N-methylacetamide in 20 ml of tetrahydrofuran, and 0.08 g (0.00099 mol) of acetyl chloride is then added and the mixture is stirred at room temperature for 1 hour. The reaction mixture is poured into 100 ml of water and extracted 3 times with in each case 50 ml of ethyl acetate. The combined organic phases are dried over magnesium sulfate and concentrated under reduced pressure. The residue is chromatographed on silica gel using cyclohexane/ethyl acetate (4:1). This gives 0.18 g (41.1% of theory) of N-(acetyloxy)-2-(2-{[6-(2-chlorophenoxy)-5-fluoro-4-pyrimidinyl]oxy} phenyl)-2-(methoxyimino)-N-methylacetamide.
HPLC: logP=3.52

The compounds of the formula (Ia) listed in Table 1 below are likewise obtained analogously to Examples 1 to 3, and in accordance with the details given in the general descriptions of processes a) and b).

TABLE 1

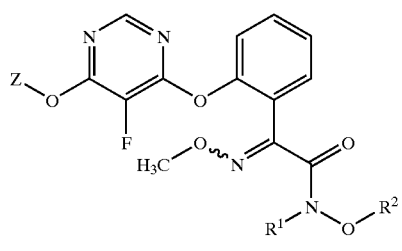

(Ia)

| Example | Z | $R^1$ | $R^2$ | log P |
|---|---|---|---|---|
| 4 | 2-fluorophenyl | —CH$_3$ | —H | 2.66 |
| 5 | 3-chloro-2-methylphenyl | —CH$_3$ | —H | 3.29 |
| 6 | 2,5-dichlorophenyl | —CH$_3$ | —H | 3.28 |
| 7 | 2,3-dichlorophenyl | —CH$_3$ | —H | 3.22 |
| 8 | 2-cyanophenyl | —CH$_3$ | —H | 2.43 |
| 9 | 2-chlorophenyl | —CH$_3$ | —CH$_3$ | 3.5 |

**) The log P values were determined in accordance with EEC directive 79/831 Annex V. A8 by HPLC (gradient method, acetonitrile/0.1% aqueous phosphoric acid)

Preparation of the Precursors

Example (II-1)

2{2-[6-(2-Chlorophenoxy)-5-fluoro-pyrimidin-4-yloxy]-phenyl)}-2-methoxyimino-acetyl chloride 50 mg of dimethylformamide are initially added to a solution of 10 g (0.024 mol) of 2-({2-[6-(2-chlorophenoxy)-5-fluoro-pyriimidin-4-yloxy]-phenyl)}-2-methoxyiminoacetic acid in 200 ml of dichloromethane, and 3.95 g (0.031 mol) of oxalyl chloride are then added dropwise. Stirring is continued at 40° C. for 5 hours and then without further input of heat for 18 hours. The reaction mixture is concentrated under reduced pressure. This gives 10.4 g (99.6% of theory) of 2-{2-[6-(2-chlorophenoxy)-5-fluoro-pyrimidin-4-yloxy]-phenyl}-2-methoxyiminoacetyl chloride.

Example (V-1)

2-1{2-[6-(2-Chlorophenoxy)-5-fluoro-pyrimidin-4-yloxy]-phenyl}-2-methoxyiminoacetic acid At −10° C., 46.4 ml (0.046 mol) of boron tribromide are added dropwise to a solution of 4 g (0.0093 mol) of methyl 2-{2-[6-(2-chlorophenoxy)-5-fluoro-pyrimidin-4-yloxy]-phenyl}-2-methoxyiminoacetate in 40 ml of dichloromethane, and the mixture is warmed to room temperature over a period of 1 hour and stirred for another 2 hours. With cooling, 300 ml of water are added dropwise, and the organic phase is then separated off. The aqueous phase is extracted two more times with in each case 100 ml of dichloromethane. The combined organic phases are filtered through kieselguhr, dried over magnesium sulfate and concentrated under reduced pressure. This gives 3.8 g (98.3% of theory) of 2-{2-[6-(2-chlorophenoxy)-5-fluoro-pyrimidin-4-yloxy]-phenyl}-2-methoxyiminoacetic acid.
NMR ([DMSO, TMS): δ=3.83 (s), 7.34–7.67 (m), 8.13 (s), 13.38 (s)

Example (VI-1)

Methyl 2-{2-[6-(2-chlorophenoxy)-5-fluoro-pyrimidin-4-yloxy]-phenyl}-2-methoxyiminoacetate 40 g (0.29 mol) of ground potassium carbonate and 58 g (0.24 mol) of 4-(2-chlorophenoxy)-5,6-difluoropyrimidine are added to a solution of 50 g (0.24 mol) of methyl 2-(2-hydroxyphenyl)-2-methoxyiminoacetate in 600 ml of acetonitrile, and the mixture is stirred at 25° C. for 18 hours. The reaction mixture is poured into 3 l of ice-water and the resulting solid is filtered off with suction. This gives 102 g (98.7% of theory) of methyl 2-{2-[6-(2-chlorophenoxy)-5-fluoro-pyrimidin-4-yloxy]-phenyl}-2-methoxyiminoacetate.
HPLC: logP=3.61

USE EXAMPLES

Example A

*Puccinia* Test (wheat)/protective

| Solvent: | 25 parts by weight of N,N-dimethylacetamide |
|---|---|
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to the control, whereas an efficacy of 100% means that no infection is observed.

In this test, the substances according to the invention mentioned in Examples (1), (4), (8) exhibit an efficacy of 95% or more at an application rate of 125 g/ha.

Example B

*Phytophthora* Test (Tomato)/Protective

| Solvent: | 24.5 parts by weight of acetone |
|---|---|
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Phytophthora infestans*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

In this test, the substances according to the invention mentioned in Examples (1), (5), (7) exhibit an efficacy of 86% or more at an application rate of 100 g/ha.

Example C

*Plasmopara* Test (Grapevine)/Protective

| Solvent: | 24.5 parts by weight of acetone |
|---|---|
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention mentioned in Examples (1), (5), (7) exhibit an efficacy of 95% or more at an application rate of 100 g/ha.

Example D

*Sphaerotheca* Test (Cucumber)/Protective

| Solvent: | 24.5 parts by weight of acetone |
|---|---|
| | 24.5 parts by weight of dimethylacetamide |
| Emulsifier: | 1.0 part by weight of alkylaryl polyglycol ether |

To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

In this test, the substances according to the invention mentioned in Examples (1), (5), (7) exhibit an efficacy of 95% or more at an application rate of 100 g/ha.

Example E
*Venturia* Test (Apple)/Protective

| Solvent: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

In this test, the substances according to the invention mentioned in Examples (1), (5) (7) exhibit an efficacy of 96% or more at an application rate 10 of g/ha.

Example F
*Pyricularia* Test (Rice)/Protective

| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated application rate. After the spray coating has dried on, the plants are inoculated with an aqueous spore suspension of *Pyricularia oryzae* and then remain at 100% rel. atmospheric humidity and 26° C. for 24 h. The plants are then placed in a greenhouse at 80% rel. atmospheric humidity and a temperature of 26° C.

Evaluation is carried out 7 days after the inoculation. 0% means an efficacy which corresponds to that of the control, whereas an efficacy of 100% means that no infection is observed.

In this test, the substances according to the invention mentioned in Examples (1), (4) (5), (7) exhibit an efficacy of 90% or more at an application rate of 250 g/ha.

Example G
ErysipheTest (Barley)/Protective

| Solvent: | 50 parts by weight of N,N-dimethylformamide |
| Emulsifier: | 1.2 parts by weight of alkylaryl polyglycol ether |

To produce a suitable preparation of active compound, 1 part by weight of active compound is mixed with the stated amount of solvent, and the concentrate is diluted with water and emulsifier to the desired concentration.

To test for protective activity, young cereal plants are sprayed with the preparation of active compound at the stated application rate. 1 day after the treatment, the plants are inoculated with spores of *Erysiphe graminis* f. sp. hordei. The plants are then placed in a greenhouse at 70% relative atmospheric humidity and a temperature of 18° C.

Evaluation is carried out 7 days after the inoculation. 0% means an efficacy which corresponds to that of the control, whereas an efficacy of 100% means that no infection is observed.

In this test, the substances according to the invention mentioned in Examples (1), (5), (7) exhibit an efficacy of 80% or more at an application rate of 750 g/ha.

What is claimed is:

1. A compound of the Formula (I)

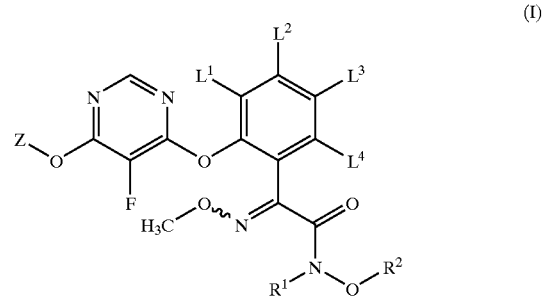

wherein

Z represents in each case substituted or unsubstituted cyoloalkyl or aryl or represents furyl, pyridyl or thienyl which is optionally substituted by methyl or thenyl, $L^1$, $L^2$, $L^3$ and $L^4$ are identical or different and independently of one another each represent hydrogen, halogen, cyano, nitro, in each case optionally halogen-substituted alkyl, alkoxy, alkylthio, alkylsulfinyl or alkylsulfonyl, $R^1$ represents hydrogen or alkyl and $R^2$ represents hydrogen, alkyl, alkylcarbonyl, alkoxycarbonyl or arylcarbonyl.

2. A compound of the Formula (I) as claimed in claim 1, wherein

Z represents cycloalkyl having 3 to 7 carbon atoms which is optionally mono- to disubstituted by halogen, alkyl or hydroxyl;

or represents phenyl or naphthyl, each of which is optionally mono- to tetrasubstituted by identical or different substituents, where the optional substituents are selected from the group consisting of:
halogen, cyano, nitro, amino, hydroxyl, formyl, carboxyl, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulfinyl or alkyfsulfonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the hydrocarbon chains;
cycloalkyl or cycloalkyloxy having in each case 3 to 6 carbon atoms;
in each case doubly attached alkylene having 3 to 4 carbon atoms, oxyalkylene having 2 or 3 carbon atoms or dioxyalkylene having 1 or 2 carbon atoms, each of which is optionally mono- to tetrasubstituted by identical or different radicals selected from the group consisting of fluorine, chlorine, oxo, methyl, trifluoromethyl and ethyl;
a grouping

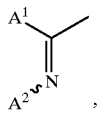

in which
$A^1$ represents hydrogen, hydroxyl or alkyl having 1 to 4 carbon atoms or cycloalkyl having 1 to 6 carbon atoms and
$A^2$ represents hydroxyl, amino, methylamino, phenyl, benzyl or represents in each case optionally cyano-, hydroxyl-, alkoxy-, alkylthio-, alkylamino, dialkylamino- or phenyl-substituted alkyl or alkoxy having 1 to 4 carbon atoms, or represents alkenyloxy or alkinyloxy having in each case 2 to 4 carbon atoms, and
phenyl, phenoxy, phenylthio, benzoyl, benzoylethenyl, cinnamoyl, heterocyclyl or phenylalkyl, phenylalkyloxy, phenylalkylthio, or heterocyclyalkyl, having in each case 1 to 3 carbon atoms in the alkyl moieties in question, each of which radicals is optionally mono- to trisubstituted in the cyclic moiety by halogen and/or straight-chain or branched alkyl or alkoxy having 1 to 4 carbon atoms,
$L^1$, $L^2$, $L^3$ and $L^4$ are identical or different and independently of one another each represent hydrogen, halogen, cyano, nitro, or alkyl, alkoxy, alkylthio, alkylsulfinyl or alkylsulfonyl having in each case 1 to 6 carbon atoms, each of which is optionally substituted by 1 to 5 halogen atoms,
$R^1$ represents hydrogen or alkyl and
$R^2$ represents hydrogen, alkyl, alkylcarbonyl, alkoxycarbonyl or arylcarbonyl.

3. A compound of the Formula (I) as claimed in claim 1, wherein
Z represents cyclopentyl or cyclohexyl, each of which is optionally mono- to disubstituted by fluorine, chlorine, methyl, ethyl or hydroxyl;
represents furyl, pyridyl or thienyl which is optionally substituted by methyl or ethyl;
or represents phenyl or naphthyl, each of which is optionally mono- to tetrasubstituted by identical or different substituents, where the optional substituents are selected from the group consisting of:
fluorine, chlorine, bromine, iodine, cyano, nitro, amino, hydroxyl, formyl, carboxyl, carbamoyl), thiocarbamoyl,
methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4,5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl,
methoxy, ethoxy, n or i-propoxy, methoxymethyl, ethoxymethyl, methylthio, ethylthio, n- or i-propylthio, methylsulfinyl, othylsulfinyl, methylsuffonyl or ethylsulfonyl, methylthiomethyl, ethykthiomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;
trifluoromethyl, trifluoroethyl,
diffluoromethoxy, trifluoromethoxy, difluorochloromethoxy, trifluoroethoxy, difluoromethylthio, trifluoromethylthio, difluorochloromethylthio, trifluoromethylsulfinyl or trifluoromethyl-sulfonyl,
methylamino, ethylamino, n- or i-propylamino, dimethylamino, diethyl-amino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl,
cyclopentyl, cyclohexyl,
in each case doubly attached propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl
a grouping

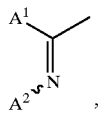

where
A¹ represents hydrogen, methyl or hydroxyl and
A² represents hydroxyl, methoxy, ethoxy, amino, methylamino, phenyl, benzyl or hydroxyethyl, and
phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3ylmethyl, triazolylmethyl, benzoxazol-2-ylmethyl, 1,3-dioxan-2-yl, benzimidazol-2-yl, dioxol-2-yl, oxadiazoly, each of which is optionally mono- to trisubstututed in the cyclic moiety by halogen and/or straight-chain or branched alkyl or alkoxy having 1 to 4 carbon atoms,
$L^1$, $L^2$, $L^3$ and $L^4$ are identical or different and independently of one another each represents hydrogen, methyl, ethyl, n- or i-propyl, n-, i-, s- or t-butyl,
$R^1$ represents hydrogen or alkyl,
$R^2$ represents hydrogen, alkyl, alkylcarbonyl, alkoxycarbonyl or arylcarbonyl.

4. A compound of the Formula (I) as claimed in claim 1, wherein
Z represents phenyl which is in each case optionally mono- to trisubstituted by identical or different substituents, where the substituents are selected from the group consisting of fluorine, chlorine, $C_1$–$C_4$-alkyl and cyano,
$L^1$, $L^2$, $L^3$ and $L^4$ represent hydrogen,
$R^1$ represents $C_1$–$C_4$-alkyl, and
$R^2$ represents hydrogen or methyl.

5. A compound of the Formula (II)

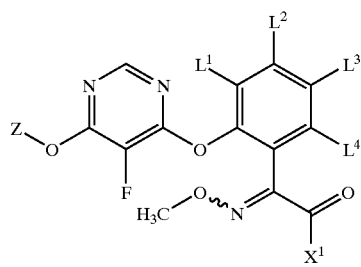

(II)

wherein
Z, $L^1$, $L^2$, $L^3$ and $L^4$ are as defined in claim 1 and
$X^1$ represents halogen.

6. A compound of the Formula (V)

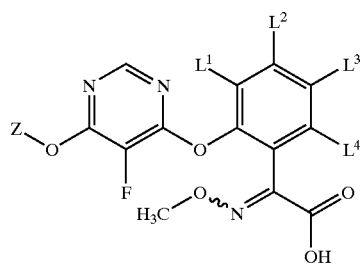

(V)

wherein
$L^1$, $L^2$, $L^3$, $L^4$ and Z are as defined in claim 1.

7. A compound of the Formula (VI)

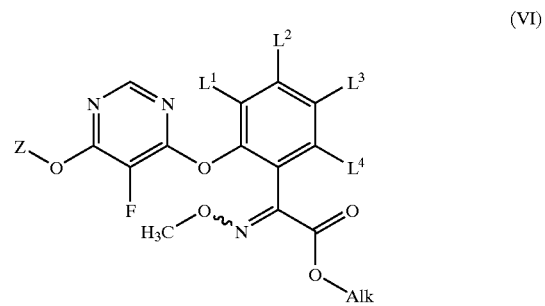

(VI)

wherein
$L^1$, $L^2$, $L^3$, $L^4$ and Z are as defined in claim 1 and
Alk represents alkyl.

8. A process for preparing a compound of the Formula (I), as defined in claim 1, comprising a step selected from the group consisting of step (a) and step (b), wherein
a) said step (a), comprises the step of reacting a carboxylic acid derivative of the Formula (II)

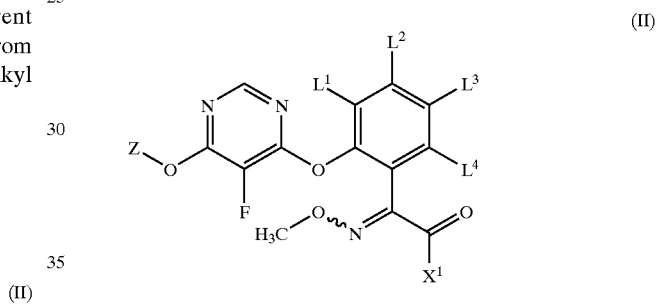

(II)

wherein
$L^1$, $L^2$, $L^3$, $L^4$ and Z are as defined in claim 1 and
$X^1$ represents halogen,
with a substituted or unsubstituted hydroxylamine derivatives of the Formula (III)

(III)

wherein
$R^1$ and $R^2$ are as defined in claim 1,
optionally in the presence of a diluent and optionally in the presence of an acid acceptor, and b) said step (b) comprises the step of reacting a compound of the Formula (I) according to claim 1, where $R^2$ is hydrogen with a halogen compound of the Formula (IV)

$X^2$—$R^{2'}$ (IV)

wherein
$R^{2'}$ represents alkyl, alkylcarbonyl, alkoxycarbonyl or arylcarbonyl and
$X^2$ represents halogen,
optionally in the presence of a diluent, optionally in the presence of an acid acceptor.

9. A composition comprising at least one compound of the Formula (I) according to claim 1 and one or more extenders and/or carriers and optionally, one or more surfactants.

10. A method for controlling pests, comprising the step of applying a member selected from the group consisting of an effective amount of a compound as defined in claim 1 and an effective amount of a composition as defined in claim 9 to a member selected from the group consisting of said pests, a habitat of said pests, and combinations thereof.

11. A process for preparing a pesticide comprising the step of mixing a compound of the Formula (I) as defined in claim 1 with one or more extenders and/or one or more surfactants.

* * * * *